(12) United States Patent
Mizutani et al.

(10) Patent No.: US 9,307,760 B2
(45) Date of Patent: Apr. 12, 2016

(54) PESTICIDAL COMPOSITION

(75) Inventors: Motofumi Mizutani, Tokyo (JP); Yumiko Kozuki, Takarazuka (JP); Maki Owaki, Osaka (JP); Masanao Takaishi, Tokyo (JP); Masato Soma, Tokyo (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 232 days.

(21) Appl. No.: 14/001,942

(22) PCT Filed: Mar. 7, 2012

(86) PCT No.: PCT/JP2012/056490
§ 371 (c)(1),
(2), (4) Date: Oct. 21, 2013

(87) PCT Pub. No.: WO2012/121413
PCT Pub. Date: Sep. 13, 2012

(65) Prior Publication Data
US 2014/0030301 A1 Jan. 30, 2014

(30) Foreign Application Priority Data

Mar. 8, 2011 (JP) ................................. 2011-049968

(51) Int. Cl.
| | | |
|---|---|---|
| *A01N 25/00* | (2006.01) | |
| *A01N 25/30* | (2006.01) | |
| *A01N 25/04* | (2006.01) | |
| *A01N 25/10* | (2006.01) | |
| *A01N 25/24* | (2006.01) | |
| *A01N 37/18* | (2006.01) | |
| *A01N 43/56* | (2006.01) | |

(52) U.S. Cl.
CPC ................ *A01N 25/30* (2013.01); *A01N 25/04* (2013.01); *A01N 25/10* (2013.01); *A01N 25/24* (2013.01); *A01N 37/18* (2013.01); *A01N 43/56* (2013.01)

(58) Field of Classification Search
CPC ....... A01N 37/38; A01N 47/16; A01N 25/04; A01N 25/10; A01N 25/24; A01N 25/30; A01N 37/18; A01N 43/56
See application file for complete search history.

(56) References Cited

U.S. PATENT DOCUMENTS

| | | | | |
|---|---|---|---|---|
| 5,250,602 A | * | 10/1993 | Itoda et al. ..................... | 524/457 |
| 2009/0093364 A1 | * | 4/2009 | Endo et al. ..................... | 504/100 |
| 2011/0306646 A1 | * | 12/2011 | Benting et al. ................. | 514/365 |

FOREIGN PATENT DOCUMENTS

| | | |
|---|---|---|
| JP | 51-151334 | 12/1976 |
| JP | 5-195493 A | 8/1993 |
| JP | 9-95640 A | 4/1997 |
| JP | 9-143001 A | 6/1997 |
| JP | 11-35408 A | 2/1999 |
| WO | WO 2005/065379 A2 | 7/2005 |
| WO | WO 2005/115413 A1 | 12/2005 |

OTHER PUBLICATIONS

The International Preliminary Report on Patentability (including a Written Opinion of the International Searching Authority (PCT/ISA/237)), dated Sep. 10, 2013, issued in International Application No. PCT/JP2012/056490.
The Notification Concerning Transmittal of International Preliminary Report on Patentability, mailed Sep. 19, 2013, issued in International Application No. PCT/JP2012/056490.
International Search Report Issued in PCT/JP2012/056490 mailed on Jul. 19, 2012.
PCT/ISA/237—Mailed on Jul. 19, 2012, issued in PCT/JP2012/056490.

* cited by examiner

*Primary Examiner* — Nannette Holloman
(74) *Attorney, Agent, or Firm* — Birch, Stewart, Kolasch & Birch, LLP

(57) ABSTRACT

The present invention relates to an aqueous pesticidal composition having excellent pesticidal activity, particularly a pesticidal composition comprising a pesticidal active ingredient, a carboxy-modified methyl methacrylate-butadiene copolymer, a surfactant and water, wherein the amount of the carboxy-modified methyl methacrylate-butadiene copolymer is 20-100 parts by weight relative to 100 parts by weight of the pesticidal active ingredient and the amount of the surfactant is 0.1-50 parts by weight relative to 100 parts by weight of the pesticidal active ingredient.

20 Claims, No Drawings

PESTICIDAL COMPOSITION

TECHNICAL FIELD

The present application is filed claiming the priority of the Japanese Patent Application No. 2011-049968, the entire contents of which are herein incorporated by the reference.

The present invention relates to a pesticidal composition, more particularly an aqueous pesticidal composition containing a pesticidal active ingredient dispersed therein.

BACKGROUND ART

Heretofore, various aqueous pesticidal compositions containing a pesticidal active ingredient are known (see, for example, JP 51-151334 A, JP 9-143001 A and JP 11-35408 A).

SUMMARY OF INVENTION

Technical Problem

An object of the present invention is to provide an aqueous pesticidal composition having improved pesticidal activity.

Solution to Problem

The present inventors have intensively studied for aqueous pesticidal compositions and finally found that an aqueous pesticidal composition containing a certain amount of a surfactant and a certain amount of a certain copolymer has improved pesticidal activity, and thus the present invention has been completed.

Namely, the present invention includes the followings:

[1] A pesticidal composition comprising a pesticidal active ingredient, a carboxy-modified methyl methacrylate-butadiene copolymer, a surfactant and water, wherein the amount of the carboxy-modified methyl methacrylate-butadiene copolymer is 20-100 parts by weight relative to 100 parts by weight of the pesticidal active ingredient and the amount of the surfactant is 0.1-50 parts by weight relative to 100 parts by weight of the pesticidal active ingredient (hereinafter referred to as "the present inventive composition").

[2] The pesticidal composition according to the above [1], comprising 1-50% by weight of the pesticidal active ingredient; 0.2-50% by weight of the carboxy-modified methyl methacrylate-butadiene copolymer; 0.1-10% by weight of the surfactant; and 20-80% by weight of water.

[3] The pesticidal composition according to the above [2], comprising 5-20% by weight of the carboxy-modified methyl methacrylate-butadiene copolymer.

[4] The pesticidal composition according to the above [2] or [3], comprising 4-6% by weight of the surfactant.

[5] The pesticidal composition according to any one of the above [1]-[4], wherein the surfactant is at least one selected from polyoxyethylene tristyrylphenyl ether phosphate esters and ligninsulfonates.

[6] The pesticidal composition according to any one of the above [1]-[5], comprising 15-25% by weight of the pesticidal active ingredient.

[7] The pesticidal composition according to any one of the above [1]-[6], wherein the pesticidal active ingredient is at least one selected from fenpyrazamine and 2-[(2,5-dimethylphenoxy)methyl]-α-methoxy-N-methyl-benzeneacetamide.

[8] The pesticidal composition according to any one of the above [1]-[7], wherein the mean particle diameter of the carboxy-modified methyl methacrylate-butadiene copolymer is 0.1-0.3 µm; the gel content of the copolymer is not less than 80% by weight; and the glass-transition temperature of the copolymer is not more than −10° C.

[9] A method for applying the pesticidal composition according to any one of the above [1]-[8], which comprises diluting the pesticidal composition according to any one of the above [1]-[8] with water, and applying the resultant water-diluted liquid to a plant by foliage spraying.

[10] A method for producing the pesticidal composition according to any one of the above [1]-[8], which comprises producing a dispersion comprising a pesticidal active ingredient, a surfactant and water, adding a carboxy-modified methyl methacrylate-butadiene copolymer to the dispersion, and uniformly dispersing the copolymer in the mixture.

[11] A method for producing the pesticidal composition according to any one of the above [1]-[8], which comprises producing a dispersion comprising a pesticidal active ingredient, a surfactant and water, adding a latex comprising a carboxy-modified methyl methacrylate-butadiene copolymer to the dispersion, and uniformly dispersing the copolymer in the mixture.

Effect of the Invention

The present inventive composition is an aqueous pesticidal composition having excellent pesticidal activity. In addition, the present inventive composition is rainfall resistant, i.e., when it is applied to a plant, the pesticidal active ingredient is hardly washed out from the plant by rainfall or watering. Therefore, the present inventive composition can sufficiently exert the pesticidal activity without being largely affected by rainfall or watering.

DESCRIPTION OF EMBODIMENTS

The present inventive composition comprises at least one pesticidal active ingredient.

The pesticidal active ingredient to be used in the present invention is not particularly limited and may be liquid or solid at room temperature (25° C.). The pesticidal active ingredient is preferably water-dispersible but not water-soluble.

The present inventive composition is an aqueous suspension composition when the pesticidal active ingredient is solid, an aqueous emulsion composition when the pesticidal active ingredient is liquid, or an aqueous emulsion-suspension composition when the pesticidal active ingredient is solid and liquid, respectively.

Examples of the pesticidal active ingredient include compounds such as insecticidal active ingredients, fungicidal active ingredients and herbicidal active ingredients, specifically the following compounds:

Insecticidal active ingredients: cypermethrin, deltamethrin, fenpropathrin, tralomethrin, acrinathrin, bifenthrin, resmethrin, tetramethrin, permethrin, isoprocarb, xylylcarb, XMC, carbaryl, carbofuran, fenoxycarb, alanycarb, fenobucarb, bendiocarb, tetrachlorvinphos, dimethylvinphos, phosalone, chlorpyrifos, chlorpyrifos-methyl, pyridafenthion, quinalphos, methidathion, azinphos-ethyl, azinphos-methyl, salithion, cyanophos, EPN, cyanofenphos, diflubenzuron, chlorfluazuron, lufenuron, hexaflumuron, flufenoxuron, flucycloxuron, diafenthiuron, hexythiazox, novaluron, teflubenzuron, triflumuron, bensultap, fenazaquin, fenpyroximate, pyridaben, hydramethylnon, thiodicarb, chlorphenapyr, pymetrozine, pyrimidifen, tebufenozide, tebufenpyrad, triazamate, sulfluramid, milbemectin, pyridalyl, buprofezin, clofentezine, fipronil, ethiprole, clothianidin, imidacloprid, thiacloprid.

Fungicidal active ingredients: S-allyl 5-amino-2,3-dihydro-2-isopropyl-3-oxo-4-(o-tolyl)pyrazol-1-carbothioate (fenpyrazamine), 2-[(2,5-dimethylphenoxy)methyl]-α-methoxy-N-methyl-benzeneacetamide, benomyl, carbendazim, thiophanate-methyl, diethofencarb, procymidone, iprodione, vinclozolin, diniconazole, tebuconazole, difenoconazole, cyproconazole, flusilazole, triadimefon, furametpyr, mepronil, flutolanil, tolclofos-methyl, pyrazophos, pyrimethanil, mepanipyrim, cyprodinil, fludioxonil, fenpiclonil, azoxystrobin, kresoxim-methyl, metominostrobin, chlorothalonil, manzeb, captan, folpet, probenazole, dimethomorph, famoxadone, oxolinic acid, fluazinam, ferimzone, thiuram, techlofthalam, carpropamid, diclocymet, tricyclazole, fthalide, trifloxystrobin, triazine, flusulfamide, diclomezine, hexaconazole.

Herbicidal active ingredients: fenoxaprop-P-ethyl, cyhalofop-butyl, bensulfuron-methyl, nicosulfuron, cyclosulfamuron, triflusulfuron-methyl, imazaquin, flumetsulam, atrazine, metribuzin, fluometuron, isoproturon, propanil, bromoxynil, ioxynil, bentazon, flumioxazin, fluthiacet-methyl, azafenidin, sulfentrazone, norflurazon, diflufenican, isoxaflutole, pendimethalin, trifluralin, mefenacet, mecoprop, fluroxypyr, simetryn, daimuron, fentrazamide, etobenzanid, swep, oxaziclomefone, oxadiazolone, pyrazolate, prodiamine, cafenstrole, pentoxazone, clomeprop, pyriftalid, benzobicyclon, bromobutide, pyraclonil, imazosulfuron, sulfosulfuron, propyrisulfuron.

The present inventive composition comprises the pesticidal active ingredient(s) in the total amount of generally 1-50% by weight, preferably 15-25% by weight.

The present inventive composition comprises at least one carboxy-modified methyl methacrylate-butadiene copolymer.

The carboxy-modified methyl methacrylate-butadiene copolymer is a methyl methacrylate-butadiene copolymer containing carboxyl group (—COOH). For the production of the present inventive composition, a latex comprising fine particles of the carboxy-modified methyl methacrylate-butadiene copolymer dispersed in water can be used. In the latex, the mean particle diameter of the fine particles of the carboxy-modified methyl methacrylate-butadiene copolymer is preferably 0.1-0.3 μm; the gel content of the copolymer is preferably not less than 80% by weight; and the glass-transition temperature of the copolymer is preferably not more than −10° C.

The "mean particle diameter" as used herein refers to a volume median diameter measured by a laser diffraction particle diameter analyzer.

The "gel content" as used herein refers to a fraction by weight of a polymer (i.e., the carboxy-modified methyl methacrylate-butadiene copolymer) insoluble in a solvent such as toluene or methyl ethyl ketone. The bigger the value is, the bigger the molecular weight of the polymer is.

The "glass-transition temperature" as used herein refers to a temperature when the polymer begins to change from a glassy to a rubbery state, which is measured by DSC (differential scanning calorimeter).

The carboxy-modified methyl methacrylate-butadiene copolymer is commercially available. Examples of the latex include NALSTAR MR-174 (trade name, manufactured by NIPPON A&L INC.).

The amount of the carboxy-modified methyl methacrylate-butadiene copolymer is 20-100 parts by weight relative to 100 parts by weight of the pesticidal active ingredient. The present inventive composition comprises the carboxy-modified methyl methacrylate-butadiene copolymer in an amount of generally 0.2-50% by weight, preferably 5-20% by weight.

The present inventive composition comprises at least one surfactant.

The surfactant to be used in the present invention may be an anionic surfactant or a nonionic surfactant.

Examples of the anionic surfactant include ligninsulfonates, alkyl naphthalene sulfonates, alkyl benzene sulfonates, dialkyl succinates, alkyl sulfate esters, polyoxyalkylene alkyl ether sulfate esters, polyoxyalkylene aryl phenyl ether sulfate esters, polyoxyalkylene alkyl ether phosphate esters, and polyoxyalkylene aryl phenyl ether phosphate esters, and examples of the salt thereof include alkali metal salts, ammonium salts and amine salts.

Examples of the nonionic surfactant include polyoxyalkylene alkyl ethers, polyoxyethylene alkyl aryl ethers, polyoxyalkylene aryl phenyl ethers, polyoxyethylene sorbitan fatty acid esters, polyoxyethylene polyoxypropylene glycols, and polyacrylate graft copolymers.

Among the surfactants, preferred are ligninsulfonates such as sodium ligninsulfonate; polyoxyethylene tristyrylphenyl ether phosphate esters such as potassium salts of polyoxyethylene tristyrylphenyl ether phosphate esters and amine salts of polyoxyethylene tristyrylphenyl ether phosphate esters; polyoxyalkylene aryl phenyl ethers; and polyacrylate graft copolymers.

The total amount of the surfactant(s) is 0.1-50 parts by weight, preferably 15-30 parts by weight, relative to 100 parts by weight of the pesticidal active ingredient. The present inventive composition comprises the surfactant(s) in the total amount of generally 0.1-10% by weight, preferably 4-6% by weight.

The present inventive composition comprises water.

The water to be used in the present inventive composition is not particularly limited, but includes those as used in a common pesticidal aqueous emulsion composition or a common pesticidal aqueous suspension composition, such as tap water, well water and ion-exchanged water.

The present inventive composition comprises water in an amount of generally 20-80% by weight, preferably 25-55% by weight.

The present inventive composition further comprises a thickening agent, an antifoaming agent, a preservative, an anti-freezing agent, and the like.

Examples of the thickening agent include organic thickening agents and inorganic thickening agents, such as xanthan gum, guar gum, gum arabic, casein, dextrin, carboxymethyl cellulose, sodium salt of carboxymethyl cellulose, sodium alginate, hydroxyethyl cellulose, carboxyethyl cellulose, methyl cellulose, hydroxypropyl cellulose, hydroxyethyl cellulose, polyvinyl alcohol, polyacrylic acid or a derivative thereof, hydrous aluminum silicate, hydrous magnesium silicate, hydrous magnesium aluminum silicate, and silica. These thickening agents may be used alone or in a mixture of two or more kinds thereof.

When the present inventive composition comprises the thickening agent(s), the total amount thereof is generally 0.1-5% by weight, preferably 0.4-0.8% by weight.

Examples of the antifoaming agent include silicone type antifoaming agents and fatty acid-type antifoaming agents.

When the present inventive composition comprises the antifoaming agent, the amount thereof is generally 0.01-3% by weight.

Examples of the preservative include butylparaben (n-butyl para-hydroxybenzoate), 5-chloro-2-methyl-4-isothiazolin-3-one (CMT), sorbic acid, potassium sorbate, p-chlorom-xylenol, 1,2-benzisothiazolin-3-one (BIT), 2-bromo-2-nitropropane-1,3-diol (BNP), and 2-methyl-4-isothiazolin-3-one (MT).

When the present inventive composition comprises the preservative, the amount thereof is generally 0.005-1% by weight.

Examples of the anti-freezing agent include ethylene glycol, diethylene glycol, glycerin, and propylene glycol.

When the present inventive composition comprises the anti-freezing agent, the amount thereof is generally 1-20% by weight.

The present inventive composition can be produced by using the pesticidal active ingredient, the carboxy-modified methyl methacrylate-butadiene copolymer, the surfactant and water, and, if necessary, the thickening agent, the antifoaming agent, the preservative, the anti-freezing agent and the like. The production method is not particularly limited.

For example, the present inventive composition may be produced by producing a dispersion comprising the pesticidal active ingredient, the surfactant and water, wherein the pesticidal active ingredient is emulsified or suspended in the dispersion (first step), and uniformly dispersing the carboxy-modified methyl methacrylate-butadiene copolymer in the dispersion (second step).

Examples of the first step include a step of adding the pesticidal active ingredient and the surfactant, and, if necessary, the antifoaming agent and the anti-freezing agent to water; dispersing the resultant mixture by using Dispermill and the like; and then fine grinding and dispersing the pesticidal active ingredient by using beads mill and the like to the mean particle diameter of the pesticidal active ingredient of not more than 10 μm, preferably not more than 5 μm.

Examples of the second step include a step of adding the carboxy-modified methyl methacrylate-butadiene copolymer, and, if necessary, the thickening agent, the preservative and the like to the dispersion obtained in the first step, and uniformly mixing the resultant mixture. In the second step, the latex comprising a carboxy-modified methyl methacrylate-butadiene copolymer may be used in addition to a carboxy-modified methyl methacrylate-butadiene copolymer itself.

The present inventive composition is applicable to places such as a paddy field, a field, an orchard, a lawn, and a non-agricultural land by using the same method as in the case of a common pesticidal aqueous emulsion composition or a common pesticidal aqueous suspension composition for controlling pests such as fungi, insects and weeds. The present inventive composition may be diluted with water, if necessary, and the resultant water-diluted liquid may be applied to a plant grown in or the soil in the above-mentioned places by spraying and the like. Examples of the spraying method for the water-diluted liquid include soil surface spraying and foliage spraying by using a known sprayer and the like.

In addition, the water-diluted liquid may be used in seed treatment, seedling raising box treatment, and the like.

The present inventive composition may be applied as it is without diluting with water, for example, by spraying from the ridge of a flooded paddy field and the like along the ridge. Before spraying, a container containing the present inventive composition is generally stirred gently to mix the present inventive composition.

EXAMPLES

Hereinafter, the present invention will be explained in more detail with reference to Production Examples and Test Examples.

Firstly, Production Examples will be described below. In the Production Examples, the following trade names are used.
NALSTAR MR-174:
  Content of carboxy-modified methyl methacrylate-butadiene copolymer: 50% by weight, water content: 50% by weight, mean particle diameter of the copolymer: 170 nm, gel content of the copolymer: 95% by weight, glass-transition temperature of the copolymer: −30° C., manufactured by NIPPON A&L INC.
Reax 83A:
  Sodium ligninsulfonate, manufactured by MeadWestvaco
Reax 85A:
  Sodium ligninsulfonate, manufactured by MeadWestvaco
Soprophor FLK:
  Potassium salt of polyoxyethylene tristyrylphenyl ether phosphate ester, manufactured by Rhodia
Step-Flow 1500:
  Polyoxyalkylene tristyrylphenyl ether, manufactured by Stepan
Dispersogen TP160T:
  Amine salt of polyoxyethylene tristyrylphenyl ether phosphate ester, manufactured by Clariant
Dispersogen PSL100:
  Polyacrylate graft copolymer, manufactured by Clariant
Kelzan S:
  Xanthane gum, manufactured by CP Kelco
Veegum Granules:
  Magnesium aluminum silicate, manufactured by Vanderbilt
Kunipia-F:
  Hydrous aluminum silicate, manufactured by Kunimine Industries Co., Ltd.
CE Antifoam Emulsion:
  Silicone type antifoaming agent, manufactured by Dow Corning
Antifoam C Emulsion:
  Silicone type antifoaming agent, manufactured by Dow Corning
KS-538
  Silicone type antifoaming agent, manufactured by Shin-Etsu Chemical Co., Ltd.
Proxel GXL:
  Preservative, manufactured by Arch Chemicals
Proxel GXL(S):
  Preservative, manufactured by Arch Chemicals
DYNO-MILL KDL:
  Horizontal bead mill, manufactured by SHINMARU ENTERPRISES CORPORATION Production Example 1

Firstly, 20 parts by weight of fenpyrazamine, 6 parts by weight of Reax 85A, 0.4 parts by weight of Kunipia-F, 0.1 parts by weight of Antifoam C Emulsion, 5 parts by weight of propylene glycol and 28.3 parts by weight of ion-exchanged water were mixed. Then, the resultant mixture was wet-ground by using DYNO-MILL KDL to obtain a suspension. To the resultant suspension were added and uniformly dispersed 0.2 parts by weight of Proxel GXL and 40 parts by weight of NALSTAR MR-174 to obtain the present inventive composition (1).

Production Example 2

Firstly, 20 parts by weight of fenpyrazamine, 6 parts by weight of Reax 83A, 0.4 parts by weight of Kunipia-F, 0.1 parts by weight of Antifoam C Emulsion, 5 parts by weight of propylene glycol and 28.3 parts by weight of ion-exchanged water were mixed. Then, the resultant mixture was wet-ground by using DYNO-MILL KDL to obtain a suspension. To the resultant suspension were added and uniformly dispersed 0.2 parts by weight of Proxel GXL and 40 parts by weight of NALSTAR MR-174 to obtain the present inventive composition (2).

Production Example 3

Firstly, 25 parts by weight of 2-[(2,5-dimethylphenoxy)methyl]-α-methoxy-N-methyl-benzeneacetamide, 4 parts by weight of Soprophor FLK, 0.25 parts by weight of Antifoam C Emulsion, 6.25 parts by weight of propylene glycol and 27.83 parts by weight of ion-exchanged water were mixed. Then, the resultant mixture was wet-ground by using DYNO-MILL KDL to obtain a suspension.

In addition, 0.2 parts by weight of Proxel GXL(S), 0.2 parts by weight of Kelzan S and 0.3 parts by weight of Veegum Granules were added to 25.97 parts by weight of ion-exchanged water, and the resultant mixture was stirred for 2 hours to obtain a uniform dispersion.

The dispersion was mixed with the above suspension. To the resultant mixture was added and uniformly dispersed 10 parts by weight of NALSTAR MR-174 to obtain the present inventive composition (3).

Production Example 4

Firstly, 20 parts by weight of 2-[(2,5-dimethylphenoxy)methyl]-α-methoxy-N-methyl-benzeneacetamide, 2 parts by weight of Soprophor FLK, 2 parts by weight of Step-Flow 1500, 0.2 parts by weight of Antifoam C Emulsion, 5 parts by weight of propylene glycol and 24.13 parts by weight of ion-exchanged water were mixed. Then, the resultant mixture was wet-ground by using DYNO-MILL KDL to obtain a suspension.

In addition, 0.2 parts by weight of Proxel GXL(S), 0.2 parts by weight of Kelzan S and 0.5 parts by weight of Veegum Granules were added to 25.77 parts by weight of ion-exchanged water, and the resultant mixture was stirred for 2 hours to obtain a uniform dispersion.

The dispersion was mixed with the above suspension. To the resultant mixture was added and uniformly dispersed 20 parts by weight of NALSTAR MR-174 to obtain the present inventive composition (4).

Production Example 5

Firstly, 25 parts by weight of 2-[(2,5-dimethylphenoxy)methyl]-α-methoxy-N-methyl-benzeneacetamide, 2 parts by weight of Soprophor FLK, 2 parts by weight of Step-Flow 1500, 0.2 parts by weight of Antifoam C Emulsion, 5 parts by weight of propylene glycol and 12.47 parts by weight of ion-exchanged water were mixed. Then, the resultant mixture was wet-ground by using DYNO-MILL KDL to obtain a suspension.

In addition, 0.2 parts by weight of Proxel GXL(S), 0.25 parts by weight of Kelzan S and 0.4 parts by weight of Veegum Granules were added to 32.48 parts by weight of ion-exchanged water, and the resultant mixture was stirred for 2 hours to obtain a uniform dispersion.

The dispersion was mixed with the above suspension. To the resultant mixture was added and uniformly dispersed 20 parts by weight of NALSTAR MR-174 to obtain the present inventive composition (5).

Production Example 6

Firstly, 15 parts by weight of 2-[(2,5-dimethylphenoxy)methyl]-α-methoxy-N-methyl-benzeneacetamide, 4 parts by weight of Soprophor FLK, 0.2 parts by weight of CE Antifoam Emulsion (manufactured by Dow Corning), 5 parts by weight of propylene glycol and 5.8 parts by weight of ion-exchanged water were mixed. Then, the resultant mixture was wet-ground by using DYNO-MILL KDL to obtain a suspension.

In addition, 0.2 parts by weight of Proxel GXL(S), 0.3 parts by weight of Kelzan S and 0.5 parts by weight of Veegum Granules were added to 39 parts by weight of ion-exchanged water, and the resultant mixture was stirred for 2 hours to obtain a uniform dispersion.

The dispersion was mixed with the above suspension. To the resultant mixture was added and uniformly dispersed 30 parts by weight of NALSTAR MR-174 to obtain the present inventive composition (6).

Production Example 7

Firstly, 25 parts by weight of 2-[(2,5-dimethylphenoxy)methyl]-α-methoxy-N-methyl-benzeneacetamide, 4 parts by weight of Dispersogen TP160T, 1 part by weight of Dispersogen PSL100, 0.2 parts by weight of Antifoam C Emulsion, 5 parts by weight of propylene glycol and 32.13 parts by weight of ion-exchanged water were mixed. Then, the resultant mixture was wet-ground by using DYNO-MILL KDL to obtain a suspension.

In addition, 0.2 parts by weight of Proxel GXL, 0.14 parts by weight of Kelzan S and 0.3 parts by weight of Veegum Granules were added to 18.03 parts by weight of ion-exchanged water, and the resultant mixture was stirred for 2 hours to obtain a uniform dispersion.

The dispersion was mixed with the above suspension. To the resultant mixture was added and uniformly dispersed 20 parts by weight of NALSTAR MR-174 to obtain the present inventive composition (7).

Production Example 8

Firstly, 25 parts by weight of 2-[(2,5-dimethylphenoxy)methyl]-α-methoxy-N-methyl-benzeneacetamide, 4 parts by weight of Dispersogen TP160T, 1 part by weight of Dispersogen PSL100, 0.2 parts by weight of KS-538, 5 parts by weight of propylene glycol and 28.47 parts by weight of ion-exchanged water were mixed. Then, the resultant mixture was wet-ground by using DYNO-MILL KDL to obtain a suspension.

In addition, 0.2 parts by weight of Proxel GXL, 0.16 parts by weight of Kelzan S and 0.32 parts by weight of Veegum Granules were added to 20.65 parts by weight of ion-exchanged water, and the resultant mixture was stirred for 2 hours to obtain a uniform dispersion.

The dispersion was mixed with the above suspension. To the resultant mixture was added and uniformly dispersed 20 parts by weight of NALSTAR MR-174 to obtain the present inventive composition (8).

Comparative Production Example 1

Firstly, 20 parts by weight of fenpyrazamine, 6 parts by weight of Reax 85A, 0.1 parts by weight of Antifoam C Emulsion, 5 parts by weight of propylene glycol and 55.57 parts by weight of ion-exchanged water were mixed. Then, the resultant mixture was wet-ground by using DYNO-MILL KDL to obtain a suspension.

In addition, 0.2 parts by weight of Proxel GXL, 0.1 parts by weight of Kelzan S and 0.2 parts by weight of Veegum Granules were added to 12.83 parts by weight of ion-exchanged water, and the resultant mixture was stirred for 2 hours to obtain a uniform dispersion.

The dispersion was mixed with the above suspension to obtain the comparative composition (1).

Comparative Production Example 2

Firstly, 30 parts by weight of 2-[(2,5-dimethylphenoxy)methyl]-α-methoxy-N-methyl-benzeneacetamide, 2 parts by weight of Soprophor FLK, 2 parts by weight of Step-Flow 1500, 0.2 parts by weight of Antifoam C Emulsion, 5 parts by weight of propylene glycol and 34.13 parts by weight of ion-exchanged water were mixed. Then, the resultant mixture was wet-ground by using DYNO-MILL KDL to obtain a suspension.

In addition, 0.2 parts by weight of Proxel GXL(S), 0.2 parts by weight of Kelzan S and 0.4 parts by weight of Veegum Granules were added to 25.87 parts by weight of ion-exchanged water, and the resultant mixture was stirred for 2 hours to obtain a uniform dispersion.

The dispersion was mixed with the above suspension to obtain the comparative composition (2).

Comparative Production Example 3

Firstly, 30 parts by weight of 2-[(2,5-dimethylphenoxy)methyl]-α-methoxy-N-methyl-benzeneacetamide, 4 parts by weight of Soprophor FLK, 0.2 parts by weight of CE Antifoam Emulsion, 5 parts by weight of propylene glycol and 34.13 parts by weight of ion-exchanged water were mixed. Then, the resultant mixture was wet-ground by using DYNO-MILL KDL to obtain a suspension.

In addition, 0.2 parts by weight of Proxel GXL(S), 0.2 parts by weight of Kelzan S and 0.4 parts by weight of Veegum Granules were added to 25.87 parts by weight of ion-exchanged water, and the resultant mixture was stirred for 2 hours to obtain a uniform dispersion.

The dispersion was mixed with the above suspension to obtain the comparative composition (3).

Comparative Production Example 4

Firstly, 25 parts by weight of 2-[(2,5-dimethylphenoxy)methyl]-α-methoxy-N-methyl-benzeneacetamide, 2 parts by weight of Soprophor FLK, 2 parts by weight of Step-Flow 1500, 0.2 parts by weight of Antifoam C Emulsion, 5 parts by weight of propylene glycol and 19.55 parts by weight of ion-exchanged water were mixed. Then, the resultant mixture was wet-ground by using DYNO-MILL KDL to obtain a suspension.

In addition, 0.2 parts by weight of Proxel GXL(S), 0.3 parts by weight of Kelzan S and 0.3 parts by weight of Veegum Granules were added to 39.2 parts by weight of ion-exchanged water, and the resultant mixture was stirred for 2 hours to obtain a uniform dispersion.

The dispersion was mixed with the above suspension. To the resultant mixture was added and uniformly dispersed 6.25 parts by weight of NALSTAR MR-174 to obtain the comparative composition (4).

Next, Test Examples will be described below.

Test Example 1

A soil was put in a plastic pot, and then seeds of rape (*Brassica napus*) were sown on the soil and grown in a glasshouse.

The present inventive compositions (3), (4) and (6) and the comparative composition (3) were diluted with water, respectively. Each water-diluted liquid was sprayed on the surface of the leaves of rape (application dosage of pesticidal active ingredient: 200 g/10000 m$^2$, and application volume of water-diluted liquid: 250 L/10000 m$^2$). After that, the surface of the leaves was dried.

Then, artificial rainfall on the rape plants was conducted by using an artificial raindrop generator manufactured by Daiki (the total amount of rainfall was 60 mm). After that, the surface of the leaves was dried. Then, a PDA medium containing the hyphae of fungus of *sclerotinia* rot of rape plant (*Sclerotinia sclerotiorum*) was inoculated on the surface of the leaves. Then, the rape plants were placed at 18° C. for 4 days under high humidity condition, and the diameter of lesions on the surface of the leaves was measured.

As a result, the diameters of lesions on the surface of the leaves sprayed with the present inventive compositions (3), (4) and (6) were 32%, 24% and 24% of that on the surface of the leaves sprayed with the comparative composition (3), respectively.

Test Example 2

The present inventive composition (5) and the comparative compositions (2) and (4) were diluted with water, respectively. Each water-diluted liquid was sprayed on the surface of the leaves of rape plants (*Brassica napus*) grown in the outside (application dosage of pesticidal active ingredient: 200 g/10000 m$^2$, and application volume of water-diluted liquid: 250 L/10000 m$^2$). Seven (7) days after the application, the treated leaves were cut and then a PDA medium containing the hyphae of fungus of *sclerotinia* rot of rape plant (*Sclerotinia sclerotiorum*) was inoculated on the surface of the leaves. Then, the leaves were placed at 20-25° C. for 3 days under high humidity condition, and the diameter of lesions on the surface of the leaves was measured.

As a result, the diameter of lesions on the surface of the leaves sprayed with the present inventive composition (5) was 50% of that on the surface of the leaves sprayed with the comparative composition (2) or 44% of that on the surface of the leaves sprayed with the comparative composition (4).

Test Example 3

A soil was put in a plastic pot, and then seeds of rape (*Brassica napus*) were sown on the soil and grown in a glasshouse.

The present inventive compositions (1) and (2) and the comparative composition (1) were diluted with water, respectively. Each water-diluted liquid was sprayed on the surface of the leaves of rape (application dosage of pesticidal active ingredient: 200 g/10000 m$^2$, and application volume of water-diluted liquid: 250 L/10000 m$^2$). After that, the surface of the leaves was dried.

Then, artificial rainfall on the rape plants was conducted by using an artificial raindrop generator manufactured by Daiki (the total amount of rainfall was 30 mm). After that, the surface of the leaves was dried. Then, a PDA medium containing the hyphae of fungus of *sclerotinia* rot of rape plant (*Sclerotinia sclerotiorum*) was inoculated on the surface of the leaves. Then, the rape plants were placed at 18° C. for 3 days under high humidity condition, and the diameter of lesions on the surface of the leaves was measured.

As a result, the diameters of lesion on the surface of the leaves sprayed with the present inventive compositions (1) and (2) were 9% and 7% of that on the surface of the leaves sprayed with the comparative composition (1), respectively.

The invention claimed is:

1. A pesticidal composition comprising a pesticidal active ingredient, a carboxy-modified methyl methacrylate-butadiene copolymer, a surfactant and water,
   wherein the amount of the carboxy-modified methyl methacrylate-butadiene copolymer is 20-100 parts by weight relative to 100 parts by weight of the pesticidal active ingredient and the amount of the surfactant is 0.1-50 parts by weight relative to 100 parts by weight of the pesticidal active ingredient, and wherein the pesticidal active ingredient and the carboxy-modified methyl methacrylate-butadiene copolymer are respectively dispersed in water.

2. The pesticidal composition according to claim 1, comprising 1-50% by weight of the pesticidal active ingredient; 0.2-50% by weight of the carboxy-modified methyl methacrylate-butadiene copolymer; 0.1-10% by weight of the surfactant; and 20-80% by weight of water.

3. The pesticidal composition according to claim 2, comprising 5-20% by weight of the carboxy-modified methyl methacrylate-butadiene copolymer.

4. The pesticidal composition according to claim 2, comprising 4-6% by weight of the surfactant.

5. The pesticidal composition according to claim 1, wherein the surfactant is at least one selected from polyoxyethylene tristyrylphenyl ether phosphate esters and ligninsulfonates.

6. The pesticidal composition according to claim 1, comprising 15-25% by weight of the pesticidal active ingredient.

7. The pesticidal composition according to claim 1, wherein the pesticidal active ingredient is at least one selected from fenpyrazamine and 2-[(2,5-dimethylphenoxy)methyl]-α-methoxy-N-methyl-benzeneacetamide.

8. The pesticidal composition according to claim 1, wherein the mean particle diameter of the carboxy-modified methyl methacrylate-butadiene copolymer is 0.1-0.3 μm; the gel content of the copolymer is not less than 80% by weight; and the glass-transition temperature of the copolymer is not more than −10° C.

9. A method for applying the pesticidal composition according to claim 1, which comprises diluting the pesticidal composition according to claim 1 with water, and applying the resultant water-diluted liquid to a plant by foliage spraying.

10. A method for producing the pesticidal composition according to claim 1, which comprises producing a dispersion comprising a pesticidal active ingredient, a surfactant and water, adding a carboxy-modified methyl methacrylate-butadiene copolymer to the dispersion, and uniformly dispersing the copolymer in the mixture.

11. A method for producing the pesticidal composition according to claim 1, which comprises producing a dispersion comprising a pesticidal active ingredient, a surfactant and water, adding a latex comprising a carboxy-modified methyl methacrylate-butadiene copolymer to the dispersion, and uniformly dispersing the copolymer in the mixture.

12. The pesticidal composition according to claim 3, comprising 4-6% by weight of the surfactant.

13. The pesticidal composition according to claim 2, wherein the surfactant is at least one selected from polyoxyethylene tristyrylphenyl ether phosphate esters and ligninsulfonates.

14. The pesticidal composition according to claim 3, wherein the surfactant is at least one selected from polyoxyethylene tristyrylphenyl ether phosphate esters and ligninsulfonates.

15. The pesticidal composition according to claim 4, wherein the surfactant is at least one selected from polyoxyethylene tristyrylphenyl ether phosphate esters and ligninsulfonates.

16. The pesticidal composition according to claim 2, comprising 15-25% by weight of the pesticidal active ingredient.

17. The pesticidal composition according to claim 3, comprising 15-25% by weight of the pesticidal active ingredient.

18. The pesticidal composition according to claim 4, comprising 15-25% by weight of the pesticidal active ingredient.

19. The pesticidal composition according to claim 5, comprising 15-25% by weight of the pesticidal active ingredient.

20. The pesticidal composition according to claim 2, wherein the pesticidal active ingredient is at least one selected from fenpyrazamine and 2-[(2,5-dimethylphenoxy)methyl]-α-methoxy-N-methyl-benzeneacetamide.

* * * * *